United States Patent [19]

Hamaguchi et al.

[11] Patent Number: 5,110,823

[45] Date of Patent: May 5, 1992

[54] PYRROLIDINE DERIVATIVES AS NOOTROPIC AGENTS

[75] Inventors: Fumiko Hamaguchi, Tokyo; Tatsuo Nagasaka, Hachioji; Rie Hakamada, Kawasaki; Einosuke Sakurai, Saitama, all of Japan

[73] Assignee: Nisshin Flour Milling Co., Ltd., Tokyo, Japan

[21] Appl. No.: 660,950

[22] Filed: Feb. 26, 1991

[30] Foreign Application Priority Data

Aug. 24, 1990 [JP] Japan .................................. 2-221208

[51] Int. Cl.$^5$ ...................... A61K 31/42; A61K 31/40; C07D 263/54; C07D 209/00
[52] U.S. Cl. .................................... 514/375; 514/387; 514/250; 548/221; 548/375; 544/252
[58] Field of Search ................. 544/252; 548/221, 302; 514/250, 375, 387

[56] References Cited

U.S. PATENT DOCUMENTS 3,901,911  8/1975  Fontanella et al. ................. 548/302
3,948,933  4/1976  Fontanella .......................... 548/302
4,582,838  4/1986  Butler et al. ........................ 548/302

OTHER PUBLICATIONS

Amnesia-Reversal Activity of a Series of Cyclic Imides, J. Med. Chem. 1987, 30, 498–503, Donald E. Butler et al.
Chemical Abstracts vol. 67, No. 5, Abst. No. 21932d (Jul. 31, 1967).

*Primary Examiner*—Joseph Paul Brust
*Assistant Examiner*—M. S. H. Gabilan
*Attorney, Agent, or Firm*—Oblon, Spivak, McClelland, Maier & Neustadt

[57] ABSTRACT

Pyrrolidine derivatives of formula (I) are disclosed.

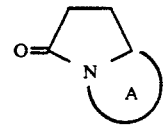

wherein the ring A represents the following heterocyclic ring

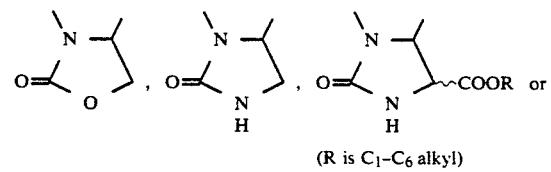

(R is $C_1$–$C_6$ alkyl)

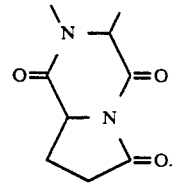

The compounds of formula (I) are useful as nootropic agents.

6 Claims, No Drawings

PYRROLIDINE DERIVATIVES AS NOOTROPIC AGENTS

FIELD OF THE INVENTION

This invention relates to new pyrrolidine derivatives, processes for preparing the same and nootropic agents comprising said derivatives as an active ingredient.

BACKGROUND OF THE INVENTION

R. Cumin et al, "Psychopharmacology (1982) 78: 104-111" discloses that 1-(p-methoxybenzoyl)-2-pyrrolidinone (aniracetam) is of an activity against amnesia.

Donald E. Butler et al, "J. Med. Chem. 1987, 30, 498-503" discloses that dihydro 1H-pyrrolizine-3,5(2H,6H)-dione possesses an amnesia reversal activity.

DISCLOSURE OF THE INVENTION

The present invention provides new compounds of formula (I)

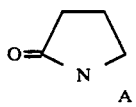

wherein the ring A represents the following heterocyclic ring

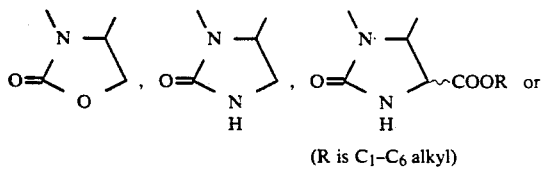

(R is C₁–C₆ alkyl)

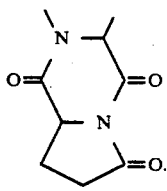

The compounds of the present invention include a stereoisomer due to an asymmetric carbon, cis, trans isomers. Thus these isomers and the mixtures thereof are also included in the scope of the present invention.

Representative of $C_1$–$C_6$ alkyl group includes methyl, ethyl, n-propyl, iso-propyl, n-butyl, sec-butyl, iso-butyl, tert-butyl, n-amyl and n-hexyl.

We have found that the compounds of formula (I) are useful as nootropic agents capable of using in the inhibition or prevention of cerebral insufficiency, improvement or therapy of amnesia, improvement, inhibition or therapy of senile dementia and improvement of intellectual capacity in such conditions as cerebral seizure and alcoholism. Thus, the present invention also provides nootropic agents comprising the compounds of formula (I) as an active ingredient.

Representative compounds of the present invention are exemplified below.

Dihydropyrrolo[2,1-c]oxazole-3,5(1H,6H)-dione

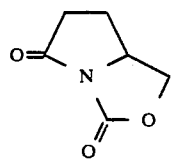

Dihydropyrrolo[2,1-c]imidazole-3,5(1H,6H)-dione

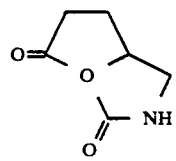

1,7a-trans-1-Methoxycarbonyl-dihydropyrrolo[2,1-c]imidazole-3,5(1H,6H)-dione

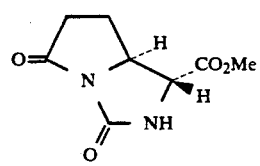

L-Pyroglutamic acid diketopiperazine

The compounds of the invention can be prepared by four methods shown in the following reaction scheme (1), (2), (3) or (4).

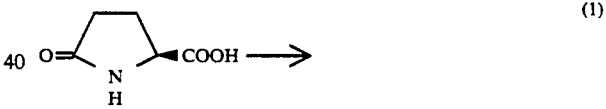  (1)

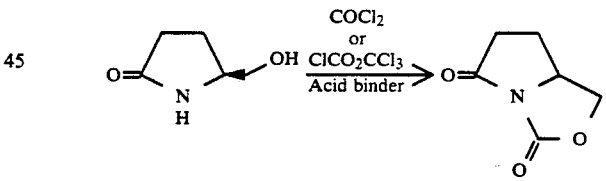

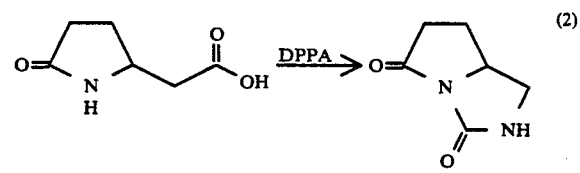  (2)

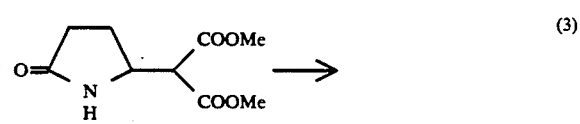  (3)

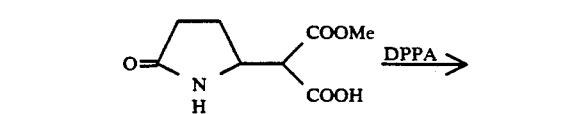

-continued

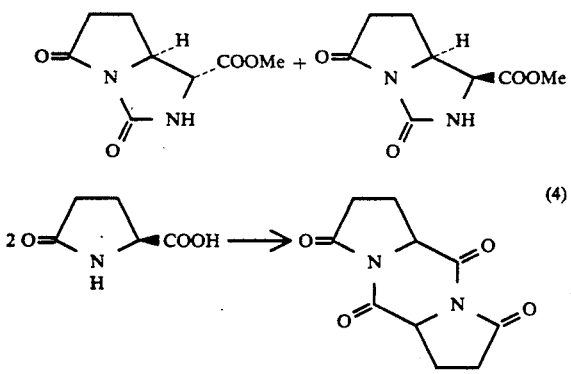

As shown in reaction scheme (1), L-pyroglutamic acid is subjected to a known reduction treatment (e.g., esterification followed by reduction) to give 5-(hydroxymethyl)-2-pyrrolidine and the resultant compound is reacted with phosgen or trichloromethyl chloroformate in the presence of an acid binder to obtain the desired compound, dihydropyrrolo[2,1-c]oxazole-3,5(1H,6H)-dione.

The reaction is carried out by esterification of L-pyroglutamic acid according to conventional methods, which include forming the acid halide followed by treatment with an alcohol or using a catalytic amount of an inorganic or organic acid in an alcohol to provide an ester followed by treating the ester with a reducing reagent (e.g., sodium borohydride) in a protonic polar solvent (e.g., an alcohol) to form an alcohol, followed by reacting the alcohol with phosgen in approximately equimolar amounts in an organic solvent (e.g., an aromatic hydrocarbon solvent) in the presence of an acid binder (e.g., an inorganic or organic base).

As shown in reaction scheme (2), 2-oxo-5-pyrrolidinyl acetic acid derived from the introduction of a carboxyl group into 5-(hydroxymethyl)-2-pyrrolidine, is reacted with diphenylphosphoryl azidate (DPPA) to obtain the desired compound, dihydropyrrolo[2,1-c]imidazole-3,5(1H,6H)-dione.

The reaction is carried out by reacting approximately equimolar amounts of 2-oxo-5-pyrrolidin-ylacetic acid, diphenylphosphoryl azidate (DPPA) and an organic base in an organic solvent such as an aromatic hydrocarbon solvent.

As shown in reaction scheme (3), methyl 2-pyrrolidinone-5-(2'-methoxycarbonyl) acetate derived from 5-ethoxy-2-pyrrolidinone is subjected to semi-hydrolysis to give 2-pyrrolidinone-5-(2'-methoxycarbonyl)acetic acid and the resultant compound is reacted with diphenylphosphoryl azidate (DPPA) to afford the desired compound, 1-methoxycarbonyldihydropyrrolo[2,1-c]imidazole-3,5(1H,6H)-dione as racemate.

The reaction is carried out by reacting approximately equimolar amounts of 2-pyrrolidinone-5-(2'-methoxycarbonyl) acetic acid derived from methyl 2-pyrrolidinone-5-(2'-methoxycarbonyl) acetate by a conventional ester hydrolysis such as alkali hydrolysis or acid hydrolysis, diphenylphosphoryl azidate (DPPA) and an organic base in an organic solvent such as an aromatic hydrocarbon solvent.

As shown in reaction scheme (4), L-pyroglutamic acid is subjected to dehydrative dimerization (by simultaneous diacylation and dehydration) to give the desired compound, L-pyroglutamic acid diketopiperazine.

The reaction is carried out by subjecting L-pyroglutamic acid to dehydrative condensation using an organic acid anhydride such as acetic anhydride. In this case, dehydrative dimerization of L-pyroglutamic acid includes diacylation to L-N,O-diacylpyroglutamic acid and simultaneous dehydration of the diacylated compound.

As previously mentioned, the compounds of formula (I) can be used for inhibition or prevention of cerebral insufficiency, improvement or therapy of amnesia, improvement, inhibition or therapy of senile dementia and improvement of intellectual capacity in such conditions as cerebral seizure and alcoholism.

The compounds of formula (I) can be formulated in various dosage forms. The pharmaceutical preparations can be administered orally in the form of tablets, sugar-coated tablets, hard capsules, soft capsules, or liquids such as solutions, emulsions or suspensions. Alternatively, the preparations may be administered rectally in the form of suppositories or parenterally in the form of injections.

These pharmaceutical preparations can be produced by known processes using additives well known in the art such as excipients, binders, dilluents, stabilizers, preservatives, solubilizers, wetting agents, emulsifiers, lubricants, sweetners, colorants, flavoring agents, buffers and antioxidants. Dosage of the present compounds is variable in a wide range, generally a daily dose of about 5 to 2500 mg/kg.

The invention is further illustrated by the following non-limitative examples.

EXAMPLE 1

Dihydropyrrolo[2,1-c]oxazole-3,5(1H,6H)-dione

To a solution of 3 g (26 mmol) of S-5-(hydroxymethyl)-2-pyrrolidinone in 60 ml of freshly distilled dichloromethane was dropwise added under ice-cooling 34.3 ml of a benzene solution of phosgen (0.113 g/ml). After completion of the addition the mixture was stirred at room temperature for 6 days. Removal of the solvent from the reaction mixture by distillation gave a brown oily residue, which was extracted with chloroform. The extract was concentrated under reduced pressure to give 8.921 g of a brown oil. Purification of the oil by column chromatography on silica gel (development solvent: dichloromethane) produced 1.327 g (yield 36.1%) of white crystals, which were recrystallized from benzene to give colorless prisms.

m.p. 137°–140° C.
$[\alpha]_D^{26} = +128.89$ (CHCl$_3$)
IR(KBr) 1800, 1730, 1710 cm$^{-1}$
Mass spectrum (m/e) 141(M+)
Elementary analysis (for C$_6$H$_7$NO$_3$)
Calc'd: C 51.06; H 5.00; N 9.93
Found: C 51.22; H 5.02; N 9.90
NMR (400MHz, CDCl$_3$) 1.97–2.10 (m,1H H-7$\beta$) 2.39–2.49 (m,1H H-7$\alpha$) 2.73 (ddd,1H, J=17.5, 8.5, 0.8Hz, H-6) 2.80–2.90 (m,1H H-6) 4.18 (dd,1H, J=8.7Hz, H-1) 4.63 (dd,1H, J=8.2Hz, H-1) 4.65–4.86 (m,1H H-7a)

EXAMPLE 2

Dihydropyrrolo[2,1-c]imidazole-3,5(1H,6H)-dione (racemate)

In 50 ml of freshly distilled toluene were dissolved under an argon stream 428 mg (3.0 mmol) of 2 -pyrrolidinone-5-acetic acid (racemate), 826 mg (3.0 mmol)

of diphenylphosphoryl azidate (DPPA) and 304 mg (3.0 mmol) of triethylamine. The mixture was heated under reflux for 20 hours. After completion of the reaction, yellowish white precipitates were collected by filtration. Recrystallization from ethanol afforded 200 mg (yield 47.3%) of pale brown needles.

m.p. 190° C.
IR(KBr) 3280, 2870, 1770, 1750, 1685 cm$^{-1}$
Mass spectrum (m/e) 140(M+)
Elementary analysis (for $C_6H_8N_2O_2$)
Calc'd: C 51.42; H 5.75; N 19.99
Found: C 51.35; H 5.76; N 20.02
NMR (400Mhz, CDCl$_3$) 1.97 (dddd,1H, J=13.13, 10.9Hz, H-7β) 2.37-2.43 (m,1H, H-7α) 2.62 (dd,1H, J=8.17Hz, H-6) 2.75 (ddd,1H, J=8.13, 17Hz, H-6) 3.33 (dd,1H, J=9.9Hz, H-1) 3.67 (dd,1H, J=9.9Hz, H-1) 4.57 (ddd,1H, J=18, 9.6Hz, H-8)

The S form was prepared from S-2-pyrrolidinone-5-acetic acid by the same procedures as above.
Yield 46.7%
m.p. 193°-195° C.
$[\alpha]_D^{26} = +71.56$ (H$_2$O)

EXAMPLE 3

1,7a-trans-1-Methoxycarbonyldihydropyrrolo-[2,1-c]imidazole-3,5(1H,6H)-dione

To 222 mg (1.1 mmol) of 2-pyrrolidinone-5-(2'-methoxycarbonyl) acetic acid was added under an argon stream 5 ml of freshly distilled tetrahydrofuran. To the mixture were dropwise added 122 mg (1.21 mmol) of triethylamine and 333 mg (1.21 mmol) of DPPA respectively added to 5 ml of freshly distilled tetrahydrofuran. The resulting mixture was heated under reflux for 5 hours, and the reaction was heated under reflux for 5 hours, and the reaction mixture was concentrated under reduced pressure. Purification of 435 mg of the residue by column chromatography on silica gel (development solvent, chloroform:methanol=30:1) afforded two diastereomers, 40 mg of a lower polar substance and 55 mg of a higher polar substance. An NOE experiment suggests that the lower polar substance is the trans form

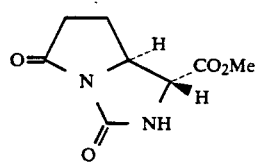

and the higher polar substance is the cis form

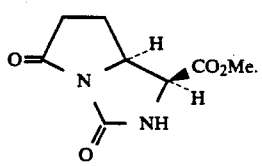

The trans form was identified as follows:
m.p. 168°-172° C.
IR(KBr) 3300, 1765, 1740, 1690 cm$^{-1}$
Mass spectrum (m/e) 199(M++1)
NMR (400MHz, CDCl$_3$) 2.04-2.18 (m,1H, H-7β) 2.40-2.51 (m,1H H-7α) 2.64 (dd,1H, J=16.5, 8.6Hz, H-6) 2.70-2.80 (m,1H, H-6) 3.84 (s,3H, COOCH$_3$) 4.24 (d,1H, J=8.3Hz, H-1) 4.49-4.56 (m,1H, H-8) 5.58 (br.s 1H, NH)

EXAMPLE 4

Diketopiperazine of L-pyroqlutamic acid

To 500 mg (3.9 mmol) of L-pyroglutamic acid was added 20 ml of freshly distilled acetic anhydride, and the mixture was heated under reflux for 6 hours. The reaction mixture was concentrated under reduced pressure, and the residue was dissolved in benzene, whereupon 64 mg of the title compound was obtained as an insoluble matter.
Yield 7.4%
m.p. >290° C.
IR(KBr) 3380, 1760, 1690 cm$^{-1}$
Mass spectrum (m/e) 222(M+)
NMR (90Mhz, D$_2$O) 2.17-2.83 (m, 8H) 4.80-5.10 (m, 2H)

Representative compounds of the invention were evaluated for an activity against amnesia using "passive avoidance" test with scopolamine-induced amnesia.

Passive Avoidance

The test apparatus was a light chamber (10×14×20 cm) and a dark chamber (24×24×20 cm) with a stainless grid floor to which an electroshock can be applied by a Co., Ltd.). The passive avoidance test was conducted on 3 groups of 10 DDY mice (male, 5 weeks age). To the animals of the first group as a control, CMC was orally administered and after 30 minutes, a solution of scopolamine in physiological saline was subcutaneously administered at a dose of 1.0 mg/kg. To other two groups, the test compounds, i.e., 1-(p-methoxybenzoyl)-2-pyrrolidinone (aniracetam) as a comparative compound and the present compounds were orally administered at doses of 30 mg/kg and after 30 minutes, a solution of scopolamine in physiological saline was subcutaneously administered at a dose of 1.0 mg/kg. 30 minutes after the subcutaneous administration, the acquisition trial was conducted and 24 hours thereafter the retention trial was conducted.

Acquisition Trial

Mice were individually placed in the light chamber at a direction opposite to the passage inlet. A latency at which the limb of a mouse completely enters the dark chamber was measured. A foot shock (1 mA, for 0.5 sec.) was delivered through the grid floor as soon as the mouse entered the dark chamber. Thereafter, each mouse was returned to a conventional case.

Retention Trial 24 hours after the acquisition trial, each mouse was again placed in the light chamber in accordance with the same procedure as done in the previous day. The latency was measured. In this case, no foot shock was given.

In the following table, the results are shown as percent change in latencies over control defined as 100.

| Effects of Compounds against Amnesia | |
|---|---|
| Test Compound | Amnesia-reversal activity (%) |
| Aniracetam | 161.3 |
| Compound of Example 2 | 310.2 |
| Control | 100.0 |

In view of the pharmacological activity the compounds of formula (I) can be used in various dosage forms depending upon the object of administration. Particular formulations are illustrated below.

Formulation Example 1 - Tablets (one tablet)

| | |
|---|---|
| Dihydropyrrolo[2,1-c]oxazole-3,5(1H,6H)-dione (Active ingredient) | 10 mg |
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct compression. The powders were formulated by a rotary tableting machine into tablets each 6 mm in diameter and weighing 100 mg.

Formulation Example 2 - Granules (one divided form)

| | |
|---|---|
| Dihydropyrrolo[2,1-c]imidazole-3,5(1H,6H)-dione (Active ingredient) | 10 mg |
| Lactose | 90 mg |
| Corn starch | 50 mg |
| Crystalline cellulose | 50 mg |
| Hydroxypropylcellulose | 10 mg |
| Ethanol | 90 mg |

The active ingredient, lactose, corn starch and crystalline cellulose were uniformly blended, to which were added a solution of hydroxypropylcellulose and ethanol. The mixture was kneaded and granulated by extrusion granulation. The granules were dried in a drier at 50° C. and screened to particle sizes of 297 μm–1460 μm. The granular formulation was divided into 200 mg per division.

Formulation Example 3 - Syrup

| | |
|---|---|
| 1,7a-trans-1-Methoxycarbonyldihydro-pyrrolo[2,1-c]imidazole-3,5(1H,6H)-dione (Active ingredient) | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavors | 0.200 g |
| Glycerin | 0.150 g |
| 96% Ethanol | 0.500 g |
| Distilled water | q.s. |
| Total | 100 ml |

Sucrose, D-sorbitol, methyl paraoxybenzoate, propyl praoxybenzoate and the active ingredient were dissolved in 60 g of warm water. To the solution, after cooling, were added glycerin and the flavors dissolved in the ethanol. To the mixture was then added water to make up 100 ml.

Formulation Example 4 - Injections

| | |
|---|---|
| Dihydropyrrolo[2,1-c]oxazole-3,5(1H,6H)-dione (Active ingredient) | 2 mg |
| CMC | 2 mg |
| Distilled water | 1 mg |

CMC and the active ingredient were suspended in distilled water to prepare an injection.

Formulation Example 5 - Suppositories

| | |
|---|---|
| Dihydropyrrolo[2,1-c]imidazole-3,5(1H,6H)-dione (Active ingredient) | 2 g |
| Polyethylene glycol 4000 | 20 g |
| Glycerin | 78 g |
| Total | 100 g |

The active ingredient was dissolved in glycerin. To the solution was added polyethylene glycol 4000, and the mixture was warmed to a solution. The solution was poured into a suppository mold and solidified by cooling to prepare suppositories weighing 1.5 g per piece.

What is claimed is:

1. A compound of formula (I)

wherein the ring A represents the following heterocyclic ring

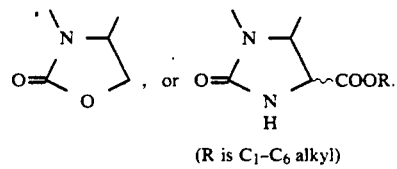

(R is $C_1$–$C_6$ alkyl)

2. A compound of claim 1 wherein the ring A represents

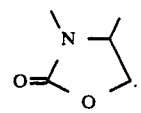

3. A compound of claim 1 wherein the ring A represents

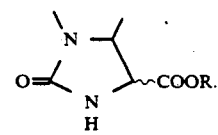

4. A nootropic agent comprising as an active ingredient a nootropic effective amount of a compound of formula (I)

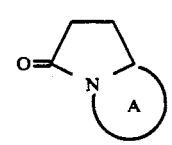

wherein the ring A represents the following heterocyclic ring

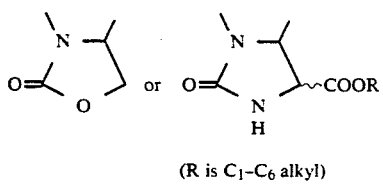
(R is $C_1$–$C_6$ alkyl)
and a pharmaceutically acceptable carrier.
5. A nootropic agent of claim 4 wherein the ring A represents
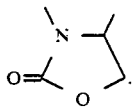
6. A nootropic agent of claim 4 wherein the ring A represents
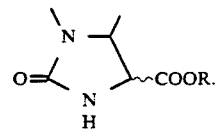
* * * * *